(12) United States Patent
Weston et al.

(10) Patent No.: US 10,222,278 B2
(45) Date of Patent: Mar. 5, 2019

(54) DIRECTIONAL FORCE SENSING ELEMENT AND SYSTEM

(71) Applicant: Massachusetts Institute of Technology, Cambridge, MA (US)

(72) Inventors: Christine M. Weston, Cambridge, MA (US); Joseph J. Lacirignola, Beverly, MA (US); David C. Maurer, Stoneham, MA (US); David F. Aubin, Jr., Pelham, NH (US); Andrew P. Dumas, Somerville, MA (US); Ninoshka K. Singh, Somerville, MA (US); Jeffrey S. Palmer, Westford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 183 days.

(21) Appl. No.: 15/386,287

(22) Filed: Dec. 21, 2016

(65) Prior Publication Data
US 2018/0010969 A1    Jan. 11, 2018

Related U.S. Application Data

(60) Provisional application No. 62/299,606, filed on Feb. 25, 2016.

(51) Int. Cl.
*G01L 1/04* (2006.01)
*A61B 5/103* (2006.01)
(Continued)

(52) U.S. Cl.
CPC .......... *G01L 1/044* (2013.01); *A61B 5/1038* (2013.01); *A61B 5/6802* (2013.01);
(Continued)

(58) Field of Classification Search
CPC ................. G01L 1/04; G01L 1/044
(Continued)

(56) References Cited

U.S. PATENT DOCUMENTS 3,572,110 A   3/1971  James et al.
3,581,403 A   6/1971  Tuttle
(Continued)

FOREIGN PATENT DOCUMENTS

BE   1008034 A6   12/1995
CA    967018 A     5/1975
(Continued)

OTHER PUBLICATIONS

RD 351042 A English Abstract Only 2 Pages, Jul. 10, 1993, Anonymous.
(Continued)

*Primary Examiner* — Benjamin R Schmitt
(74) *Attorney, Agent, or Firm* — Daly, Crowley, Mofford & Durkee, LLP

(57) ABSTRACT

A directional force sensor and sensing system are described. The directional force sensor includes a leaf spring and one or more load sensors disposed about the leaf spring such that in response to a force applied to the leaf spring, the one or more load sensors provide a signal. A controller is coupled to receive signals from the one or more directional force sensors and determines characteristics of forces applied to the directional force sensors.

17 Claims, 6 Drawing Sheets

(51) Int. Cl.
*A61B 5/00* (2006.01)
*G01L 1/22* (2006.01)
*G01G 19/414* (2006.01)

(52) U.S. Cl.
CPC ....... *A61B 5/7225* (2013.01); *G01G 19/4142* (2013.01); *G01L 1/2268* (2013.01); *A61B 2562/0261* (2013.01)

(58) Field of Classification Search
USPC ...... 73/862.621, 862.629, 862.636, 862.637, 73/862.642
See application file for complete search history.

(56) References Cited

U.S. PATENT DOCUMENTS

| | | | |
|---|---|---|---|
| 3,626,347 | A | 12/1971 | Lawford et al. |
| 3,628,394 | A | 12/1971 | Keatinge et al. |
| 3,722,264 | A | 3/1973 | Talmo et al. |
| 3,802,258 | A | 4/1974 | Clarke et al. |
| 3,803,706 | A | 4/1974 | Talmo |
| 3,805,377 | A | 4/1974 | Talmo et al. |
| 3,910,106 | A | 10/1975 | Brady |
| 3,953,920 | A | 5/1976 | Endo |
| 4,091,680 | A | 5/1978 | Block |
| 4,162,628 | A | 7/1979 | Oetjen et al. |
| 4,164,263 | A | 8/1979 | Heintz et al. |
| 4,185,495 | A | 1/1980 | Rauch et al. |
| 4,215,754 | A | 8/1980 | Hagedorn et al. |
| 4,253,326 | A | 3/1981 | Munnich et al. |
| 4,290,303 | A | 9/1981 | Harman et al. |
| 4,385,525 | A | 5/1983 | Phillips et al. |
| 4,393,698 | A | 7/1983 | Pietzsch et al. |
| 4,411,159 | A | 10/1983 | Spear et al. |
| 4,695,963 | A * | 9/1987 | Sagisawa ............... B25J 13/081 414/5 |
| 4,762,006 | A * | 8/1988 | Asakawa ................ G01L 1/044 73/862.044 |
| 4,864,853 | A | 9/1989 | Grunder et al. |
| 4,935,683 | A | 6/1990 | Kobler et al. |
| 5,058,918 | A | 10/1991 | Nakaya et al. |
| 5,123,280 | A | 6/1992 | Baechler |
| 5,129,265 | A | 7/1992 | Bartels et al. |
| 5,174,403 | A | 12/1992 | Geiger |
| 5,212,657 | A | 5/1993 | Uchikawa et al. |
| 5,217,355 | A | 6/1993 | Hyman et al. |
| 5,257,550 | A | 11/1993 | Montalvo, III et al. |
| 5,277,072 | A | 1/1994 | Ort |
| 5,327,791 | A | 7/1994 | Walker |
| 5,410,109 | A | 4/1995 | Tarter et al. |
| 5,696,345 | A | 12/1997 | Nordelius |
| 5,989,222 | A | 11/1999 | Cole et al. |
| 6,282,814 | B1 | 9/2001 | Krafsur et al. |
| 6,595,570 | B2 | 7/2003 | Susko |
| 6,769,315 | B2 | 8/2004 | Stevenson et al. |
| 7,294,793 | B2 | 11/2007 | Axakov et al. |
| 7,427,744 | B2 | 9/2008 | Watanabe |
| 7,600,437 | B2 | 10/2009 | Brunner |
| 8,212,158 | B2 | 7/2012 | Wiest |
| 8,502,776 | B2 | 8/2013 | Kamentser et al. |
| 2006/0265174 | A1* | 11/2006 | Doyle .................... G01K 1/026 702/130 |
| 2014/0200834 | A1 | 7/2014 | Ross |

FOREIGN PATENT DOCUMENTS

| | | |
|---|---|---|
| CA | 967391 A | 5/1975 |
| CA | 1105505 A | 7/1981 |
| CH | 600892 A | 6/1978 |
| CN | 204269224 U | 4/2015 |
| DE | 2414109 A | 10/1975 |
| DE | 2719712 A | 11/1978 |
| DE | 2819603 A | 11/1979 |
| DE | 3039712 A | 5/1982 |
| DE | 3230011 A | 2/1984 |
| DE | 213320 A | 9/1984 |
| DE | 217315 A | 1/1985 |
| DE | 3534712 A | 4/1987 |
| DE | 3913648 C | 1/1990 |
| DE | 4016872 A | 11/1991 |
| DE | 4209668 A1 | 9/1993 |
| DE | 4211715 A1 | 10/1993 |
| DE | 4319080 A1 | 12/1993 |
| DE | 4228307 A1 | 3/1994 |
| DE | 4233393 A1 | 4/1994 |
| DE | 4443716 A1 | 6/1996 |
| DE | 29806179 U1 | 10/1998 |
| DE | 19910003 A1 | 9/2000 |
| DE | 19905493 A1 | 1/2001 |
| DE | 19932962 A1 | 1/2001 |
| DE | 10018942 A1 | 10/2001 |
| DE | 10154340 A1 | 5/2003 |
| DE | 10225901 | 1/2004 |
| DE | 10347843 | 4/2005 |
| EP | 848313 A2 | 6/1998 |
| EP | 1067012 A2 | 1/2001 |
| EP | 2778600 A1 | 9/2014 |
| FR | 2594148 A | 8/1987 |
| GB | 1506377 A | 4/1978 |
| GB | 1525299 A | 9/1978 |
| GB | 1535766 A | 12/1978 |
| GB | 2122748 A | 6/1982 |
| GB | 2121185 A | 12/1983 |
| GB | 2159283 A | 11/1985 |
| GB | 2178180 A | 2/1987 |
| GB | 2320932 A | 7/1998 |
| JP | 2078924 A | 3/1990 |
| JP | 3025915 A | 2/1991 |
| JP | 5227766 A | 9/1993 |
| JP | 2003028789 A | 1/2003 |
| JP | 2005090989 A | 4/2005 |
| JP | 2005127776 A | 5/2005 |
| JP | 2007034937 A | 2/2007 |
| JP | 2011068239 A | 9/2009 |
| JP | 2012078266 | 4/2012 |
| JP | 2012103153 A | 5/2012 |
| JP | 2014116184 A | 6/2014 |
| KR | 1991002927 B1 | 5/1991 |
| KR | 2004043510 A | 5/2004 |
| KR | 455038 B | 11/2004 |
| NL | 199300067 A | 8/1994 |
| RU | 2294178 C2 | 2/2007 |
| SU | 497012 A | 3/1976 |
| SU | 513281 A | 5/1976 |
| SU | 574654 A | 9/1977 |
| SU | 611154 A | 5/1978 |
| SU | 668678 A | 6/1979 |
| SU | 670977 A | 6/1979 |
| SU | 715922 A | 2/1980 |
| SU | 779848 B | 11/1980 |
| SU | 807155 B | 2/1981 |
| SU | 808919 B | 2/1981 |
| SU | 855376 B | 8/1981 |
| SU | 1203390 A | 1/1986 |
| SU | 1244515 A | 7/1986 |
| SU | 1629772 A | 2/1991 |
| SU | 1668493 | 8/1991 |
| SU | 1760402 A1 | 9/1992 |
| WO | WO 1990001143 A | 2/1990 |
| WO | WO 2003004334 A1 | 1/2003 |

OTHER PUBLICATIONS

Report Information from ProQuest Dialog dated Dec. 23, 2015 09:37 By Robert G Hall, 4 pages.
Report Information from ProQuest Dialog dated Dec. 23, 2015 09:44 By Robert G Hall; 4 pages.
Report Information from ProQuest Dialog dated Dec. 23, 2015 09:51 By Robert G Hall, 7 pages.
Anonymous; "Improved leaf springs"; Automobile Engineer 50.2; pp. 58-59; Feb. 1960; Abstract Only; 1 Page.

(56) References Cited

OTHER PUBLICATIONS

Bangert, et al.; "Ultramicrohardness-tester for thin films"; Acta Physica Academiae Scientiarum Hungaricae; Oct. 22-25, 1979; English Abstract Only; 1 Page.
Bangert, et al.; "Ultramicrohardness Tester for Use in a Scanning Electron Microscope"; Colloid and Polymer Science 259.2; pp. 238-240; Jan. 1, 1981; English Abstract Only; 1 Page.
Bangert, et al.; "Ultramicrohardness inverstigation of single crystals in a scanning electron microscope and X-ray topography of the deformation zone"; Fifth International Thin Films Congress; Sep. 21-25, 1981; English Abstract Only; 1 Page.
Chilcoat, et al.; "A measuring laryngoscope handle: A device for measuring the forces applied during laryngoscopy" Medical and Biological Engineering and computing 21.4; pp. 525-527; Jan. 1, 1983; English Abstract Only; 1 Page.
Ciaccio, et al.; "Measurement and monitoring of electrocardiogram belt tension in premature infants for assessment of respiratory function"; BioMedical Engineering Online 6; Apr. 19, 2007; English Abstract Only; 1 Page.
Heeg, et al.; "Attenuation of empennage buffet response through active conrol of damping using plezoelectric material"; National Aeronautics and Space Administration; Aug. 1993; Abstract Only; 1 Page.
Fleischmann,; "A Study of the increase in drag on cylinders due to vortex induced vibrations" 1982; Abstract Only; 1 Page.
Hellemans, et al.; "The tension in the string of a simple pendulum"; Conference on Computers in Physics Instruction; Aug. 1-5, 1988; English Abstract Only; 1 Page.
Hellemans, et al.; "Measurement of the tension in a string"; Conference on Computers in Physics Instruction; Aug. 1-5, 1988; English Abstract Only; 1 Page.
Ivers-Tiffee, et al.; "High-temperature extensometer for series inspection"; June; English Abstract Only; 1 Page.
Lee, et al.; "Design of six-component F?T sensor with flexible fixed ends"; Transactions of the Korean Society of Mechanical Engineers, A 34.6; pp. 771-780; Jun. 1, 2010; English Abstract Only; 1 Page.
Liu, et al.; "Investigation about the effect of angle of attack and relative humidity on wheel squeal" Australian Acoustic SocietyConference 2011: Breaking New Ground, Acoustics 2011; pp. 569-575; Nov. 2-4, 2011 ; English Abstract Only; 2 Pages.
Oh, et al.; "Friction and wear characteristics for automotive leaf spring materials due to the influence of the residual stress"; Advances in Fracture and Strength, PTS 1-4; Oct. 6-8, 2004; English Abstract Only; 1 Page.
Pakkratok, et al.; "Combination of VCA based micro force generator and micro robot for micro hardness and stiffness test"; Proceedings of the SICE Annual Conference; Nov. 30, 2010; English Abstract Only; 2 Pages.
Pakkratok, et al.; "Compact micro force generator with tandem leaf spring and VCA on micro robot for micro hardness and stiffness test"; 21st Conference on Measurement of Force, Mass and Torque Together with HARDMEKO 2010 and 2nd meeting on Vibration Measurement, IMEKO TC3, TC5 and TC22 Conferences; Dec. 1, 2010; English Abstract Only; 2 Pages.
Pakkratok, et al.; "Development of microscopic hardness and stiffness investigation with micro robot"; Journal of Robotics and Mechatronics 24.1; pp. 123-132; Feb. 1, 2012; English Abstract Only; 2 Pages.
Prisecariu, et al.; "Control of XY electromagnetic positioning stage" Studies in Informatics and Control 16.3; pp. 255-264; Sep. 2007; English Abstract Only; 2 Pages.
Radwin; "Computer key switch force-displacement characteristics and short-term effects on localized fatigue"; Ergonomics 42.1; pp. 160-170; Jan. 1999; English Abstract Only; 1 Page.
Roberston, et al.; "Collision-Avoidance of flying locusts—Steering torques and Behavior"; Journal of Experimental Biology; pp. 35-60; Oct. 1993; English Abstract Only; 1 Page.
Rowland; "Modern leaf spring design"; Automotive Industries 105.12; pp. 38-40; Dec. 15, 19851; English Abstract Only; 1 Page.
Sato, et al.; "Active parallel leaf spring mechanism"; Journal of the Japan Society for Precision Engineering 58.8; pp. 1381-1386; Dec. 1, 1992; English Abstract Only; 2 Pages.
Schmutz; "A strain gage switch for PWR environment"; Proceedings of the 22nd International Instrumentation Symposium; May 25-27, 1976; English Abstract Only; 1 Page.
Seki; "A parallel leaf spring structure driven by plezoelectric bimorph actuators"; Joint Japan/U.S. Conference on Adaptive Structures, 2nd, Nagoya, Japan: United States; Nov. 12-14, 1991; English Abstract Only; 1 Page.
Smaga; "Investigating the forces and displacements at the poles of automatic circuit breakers during short circuits"; Elektotekhnika 3; pp. 31-33; Mar. 1965; English Abstract Only; 1 Page.
Soner; "Leaf spring design considering natural frequency calculations based on NVH"; SAE Technical Papers; Jun. 25, 2013; English Abstract Only; 2 Pages.
Terrell, et al.; "An instrumented pencil for psychomotoric studies"; Proceedings of the Fifth National Biomedical Sciences Instrumentation Symposium; pp. 159-163; May 15-17, 1967; Abstract Only; 1 Page.
Townson; "A strain gauge 'rosette' for open channel flow"; Control 11; pp. 488-489; Oct. 1967; Abstract Only; 1 Page.
Uchida, et al.; In process measurement and workpiece-referred form accuracy contol.II. The application of K-HIPOSS and a parallel leaf-spring micro tool servo; Journal of the Japan Society of Precision Engineering; pp. 134-139; Jan. 1990; English Abstract Only; 1 Page.
Yang; "Automatic measurement of payload for heavy vehicles using strain gages"; Measurement 41.5; pp. 491-502; Jun. 2008; English Abstract Only; 1 Page.
Yuxin, et al.; "A Cr—N film displacement sensor for precision positioning of micro-stage"; Sensors and Actuators A (Physical) 211; pp. 88-97; May 1, 2014; English Abstract Only; 2 Pages.
PCT Search Report and Written Opinion of the ISA for PCT/US2016/067978 dated Feb. 28, 2017; 10 Pages.
PCT International Preliminary Report on Patentability dated Sep. 7, 2018 for International Application No. PCT/US2016/067978; 8 Pages.

* cited by examiner

DIRECTIONAL FORCE SENSING ELEMENT AND SYSTEM

CROSS-REFERENCE TO RELATED APPLICATIONS

This application claims the benefit of U.S. provisional application No. 62/299,606, filed on Feb. 25, 2016, which application is hereby incorporated herein by reference in its entirety.

STATEMENT REGARDING FEDERALLY SPONSORED RESEARCH OR DEVELOPMENT

This invention was made with Government support under Contract No. FA8721-05-C-0002 awarded by the United States Air Force. The Government has certain rights in the invention.

BACKGROUND

Musculoskeletal injuries (MSI) to the lower limbs are a pervasive modern health problem, especially in the military. Recent studies indicate that members of the military ("service members") experience hundreds of thousands of lower body MSI injuries annually, making such injuries a leading cause of lost duty days. One source of lower body MSI injury may be overburden during sustained marches. However, measuring real-world static and dynamic loads of service members is difficult, making the quantification of performance degradation and MSI due to overload in the field impossible. Measurement of the degree of overburden before, during and after missions may enable more efficient planning and combat effectiveness, reduce service member injuries, and allow improved designs for clothing, footwear, and other equipment. Therefore, improved load sensing and tracking systems are envisioned to accurately quantify both static and dynamic load outside of laboratory settings.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect of the concepts sought to be protected herein, a directional force sensing element is provided from a flexible leaf spring (e.g. a metal wave washer) having with strain gages coupled thereto. A rigid-flex circuit is suspended in a central portion of the flexible leaf spring with flexible arms extending out to the wave washer and a flexible tail to connect the board to other circuitry. The strain gages are affixed to the ends of the flexible arms. The rigid center of the wave washer contains circuitry for reading the analog strain gage values and converting them to digital values.

In accordance with another aspect of the concepts sought to be protected herein, an apparatus for measuring a directional force includes a leaf spring, one or more load sensors disposed about the leaf spring and disposed on the leaf spring such that in response to a force applied to the leaf spring, the one or more load sensors provide a signal at an output thereof and an analog-to-digital converter (ADC) coupled to receive signals from the one or more load sensors wherein a digital output of each channel of the ADC is employed to determine a magnitude and a direction of a force applied to the directional force sensor.

The above apparatus may include one or more of the following features in any combination: the leaf spring may be provided having an undulating surface; the leaf spring may be provided having a closed shape, an open shape or a linear shape; the leaf spring may be provided having a generally oval shape; the leaf spring is provided having a generally circular shape; the one or more load sensors may be disposed on a surface of the leaf spring; the one or more load sensors may be disposed about a perimeter of the leaf spring; the leaf spring may be provided as a wave washer having an undulating surface; the one or more load sensors may be disposed on a wave washer so as to form a directional force sensor; a force applied to the directional force sensor may comprises either or both of perpendicular and shear forces; each load sensor may be coupled to a separate channel of an analog to digital converter (ADC); the one or more load sensors may comprise one or more strain gages; and each of the one or more strain gages may be provided having a base resistance value and the apparatus further comprises a compensation resistor coupled to an ADC, where the compensation resistor has a value selected to compensate for the base resistance value of each strain gage, thereby measuring only a change in resistance of each strain gage as force is applied to each strain gage.

In accordance with yet another aspect of the concepts sought to be protected herein, a system comprises a directional force sensor provided from a leaf spring and one or more load sensors disposed about the leaf spring such that in response to a force applied to the leaf spring, the one or more load sensors provide a signal at an output thereof. The system further comprises an analog-to-digital converter (ADC) coupled to receive signals from the one or more load sensors of the directional force sensor and a controller coupled to the directional force sensor.

The above system may include one or more of the following features in any combination: the directional force sensor is a first one of a plurality of directional force sensors, each of the directional force sensors provided from a leaf spring, and one or more load sensors disposed about the leaf spring such that in response to a force applied to the leaf spring, the one or more load sensors provide a signal at an output thereof; an aggregator, coupled between each of the directional force sensors and the controller, and configured to batch data from the one or more directional force sensors for communication to the controller; the controller comprises one or more sensors, each of the one or more sensors responsive to environmental conditions of the controller; the one or more sensors comprise at least one of: a temperature sensor, a humidity sensor, a magnetometer, a gyrometer, one or more accelerometers, one or more motion sensors, a global positioning system, and an altimeter; the directional force sensor is disposed in footwear to sense a force applied to a sole of the footwear; the controller is configured to determine at least one of a stride data of a wearer of the footwear, a ground reaction force applied to the footwear, a foot-to-ground contact time of the footwear, a terrain map of terrain encountered by the wearer of the footwear, a contact angle of the footwear to the ground, a flexion angle of a leg of the wearer of the footwear, and an energy expenditure of the wearer of the footwear; and the directional force sensor is implemented in at least one of a backpack, a mattress, a wheelchair, a CPR simulator, sports equipment, car seat, parachute, seatbelt, steering wheel, vehicle bumper, bridge support, footwear and anthropomorphic test devices.

BRIEF DESCRIPTION OF THE DRAWING FIGURES

Aspects, features, and advantages of the concepts, systems, circuits and techniques described herein will become more fully apparent from the following detailed description, the appended claims, and the accompanying drawings in which like reference numerals identify similar or identical elements. Reference numerals that are introduced in the specification in association with a drawing figure may be repeated in one or more subsequent figures without additional description in the specification in order to provide context for other features. Furthermore, the drawings are not necessarily to scale, emphasis instead being placed on the concepts disclosed herein.

DETAILED DESCRIPTION

Described embodiments provide a directional force sensing element to measure a direction and a magnitude of static and dynamic forces applied to the sensing element. As will be described, some embodiments of the directional force sensing element sense the directionality of an applied force and sense both perpendicular and shear forces. Thus, described embodiments may be useful to a wide variety of applications including backpack load sensing, pressure sensing in mattresses and wheelchairs, sensing of chest compression force and detection in a CPR simulator or mannequin, an anthropomorphic test device (e.g., a crash test dummy), sports equipment impact detection (e.g., helmet, bat or stick impact testing), car seat weight sensing, parachute force detection, seatbelt force detection during a car accident, steering wheel grip sensing, bumper impact sensing, package transport force detection, bridge support weight measurement, footwear load sensing and other similar load sensing or impact testing applications that may experience both perpendicular and shear forces.

Figure 1:
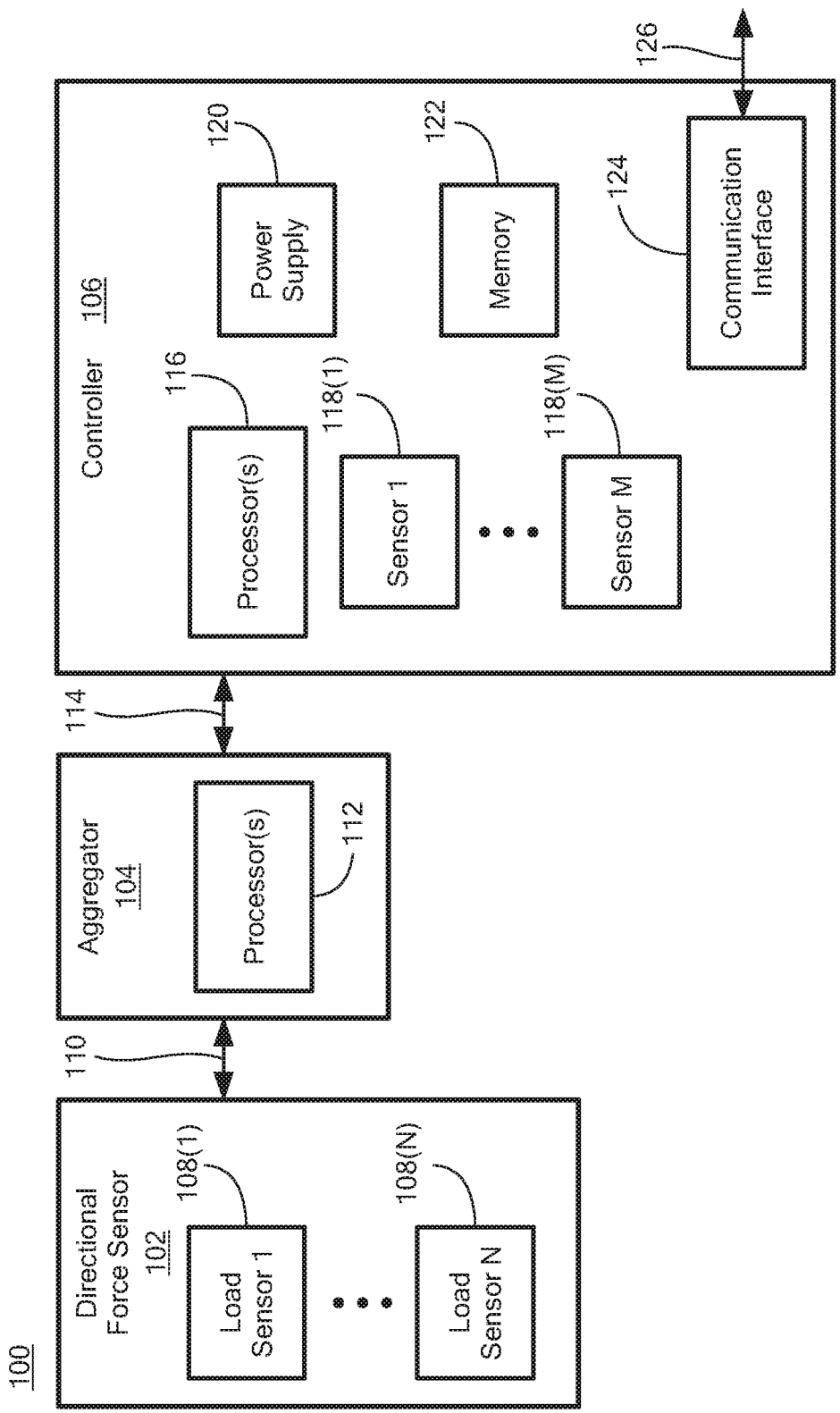
FIG. 1 is a block diagram of a directional force sensing system.

Referring now to FIG. 1, an illustrative directional force sensing system 100 includes one or more directional force sensors 102 coupled to an aggregator 104 via communication link 110. Thus, at appropriate points in time (which in some embodiments may be continuously), one or more directional force sensors 102 provide information to aggregator 104.

Aggregator 104 may combine signals from the one or more directional force sensors 102 for communication to controller 106 via communication link 114. Aggregator 104 may include one or more processors 112 to receive, process and transmit data between directional force sensors 102 and controller 106. In some embodiments, one or both of communication links 110 and 114 may be wireless links. For example, one or both of communication links 110 and 114 may be implemented as links of a personal area network (PAN), such as an IEEE 802.15 (e.g., Bluetooth®) wireless link. In other embodiments, one or both of communication links 110 and 114 may be wired links. For example, link 110 may be implemented as a serial peripheral interface (SPI) link, or other similar types of communication links.

As illustrated in FIG. 1, each directional force sensor may include one or more load sensors, shown as load sensors 108(1)-108(N), and referred to generally as load sensors 108. As will be described, load sensors 108 may sense perpendicular and shear forces applied thereto. Data associated with the forces sensed by sensors 108 may be transmitted, via communication link 110, to aggregator 104, which may combine, batch, or otherwise process data from sensors 108 for transmission, via communication link 114, to controller 106.

Should the viscoelastic modeling and calibration be mentioned? Controller 106 may receive force data from directional force sensors 102, via aggregator 104, and further process the data (e.g. by first storing the data in a storage device and then processing the data in a processor). For example, as shown in FIG. 1, controller 106 may include one or more of: a power supply 120; a processor(s) 116 and a storage device 122 (e.g. a random access memory, or non-volatile memory including, but not limited to an secure digital (SD) memory card and/or a flash memory card) for later off-loading information (including measured data or any other information) from the device).

In some embodiments, aggregator 104 may not be employed, and instead controller 106 may be in direct communication with each of the one or more directional force sensors 102. In other embodiments, controller 106 and aggregator 104 may be implemented as a single device (e.g. as part of a single integrated circuit) and/or directional forced sensor and aggregator 104 may be provided as a single device.

Controller 106 may be deployed remotely along with aggregator 104 and directional force sensors 102. For example, in some embodiments, a first directional force sensor 102 may be disposed, for example in a sole of a shoe, to sense foot and leg impact of an athlete or soldier. Additional directional force sensors may also be disposed, for example to sense a force of an impact to a helmet of the athlete or soldier, to sense a force of impact to padding or armor of the athlete or soldier, etc. Each of the directional force sensors may be in communication with controller 106. In some embodiments, the directional force sensor 1-2 may be in communication with controller 106 via aggregator 104, for example.

Further, controller 106 may include one or more sensors 118(1)-118(M), referred to generally as sensors 118, for sensing additional environmental conditions of directional force sensing system 100. For example, sensor 118 may include a temperature sensor, a humidity sensor, a gyrometer, a magnetometer, one or more accelerometers and/or motion sensors, an altimeter, a global positioning system (GPS) or portions thereof. Other sensors to sense an environment or a characteristic of an environment in which directional force sensing system 100 is disposed may also be used. Of course, in some embodiments, such additional sensors may be included as part of directional force sensor 102.

For example, when directional force sensor 102 is implemented in footwear, the force data in combination with data from the additional sensors 118 may enable controller 106 to determine stride data of a wearer of the footwear, a ground reaction force applied to the footwear, a foot-to-ground contact time of the footwear, a terrain map of terrain encountered by the wearer of the footwear, a contact angle of the footwear to the ground, a flexion angle of a leg of the wearer of the footwear, and an energy expenditure of the wearer of the footwear. Particularly, in one embodiment, directional force sensor 102 may be implemented in footwear, while aggregator 104 may be implemented as an ankle-mounted device. For example, in some embodiments, aggregator 104 may provide power to directional force sensor 102, and aggregator 104 may include one or more additional sensors (not shown) to determine, for example, a flexion angle of a leg or ankle of the wearer of the footwear. Further, in some embodiments, controller 106 may be implemented as a belt-mounted or backpack carried device (e.g., to allow for a larger power source, additional processing power, wireless communications of data to a remote processing site, etc.

Memory 122 may be employed to store data, for example data sent to controller 106 from directional force sensors 102 (e.g., via aggregator 104) and/or sensors 118. Communication interface 124 may allow controller 106 to provide data from memory 122 for further processing via communication link 126. For example, in some embodiments, communication link 126 may be implemented as a communication port to allow a wired link to download data from memory 122. In other embodiments, communication link may be implemented as wireless link to allow controller 106 to communicate to a remote data processing device. For example, in some embodiments, communication interface 126 may be implemented as a personal area network (PAN), such as an IEEE 802.15 (e.g., Bluetooth®) wireless link, an IEEE 802.11 (e.g., Wi-Fi) wireless link, a cellular link, or other similar wireless links to allow controller 106 to communicate with a remote data processing device.

Power supply 120 may include a battery or other portable power source and other components, such as voltage regulators or converters, to provide suitable electrical power for components of controller 106. In embodiments where communication links 110 and 114 are implemented as wired links, power supply 120 may also provide power (e.g., a positive power supply signal and a circuit common or negative power supply signal) to aggregator 104 and/or directional force sensors 102.

Figure 2:
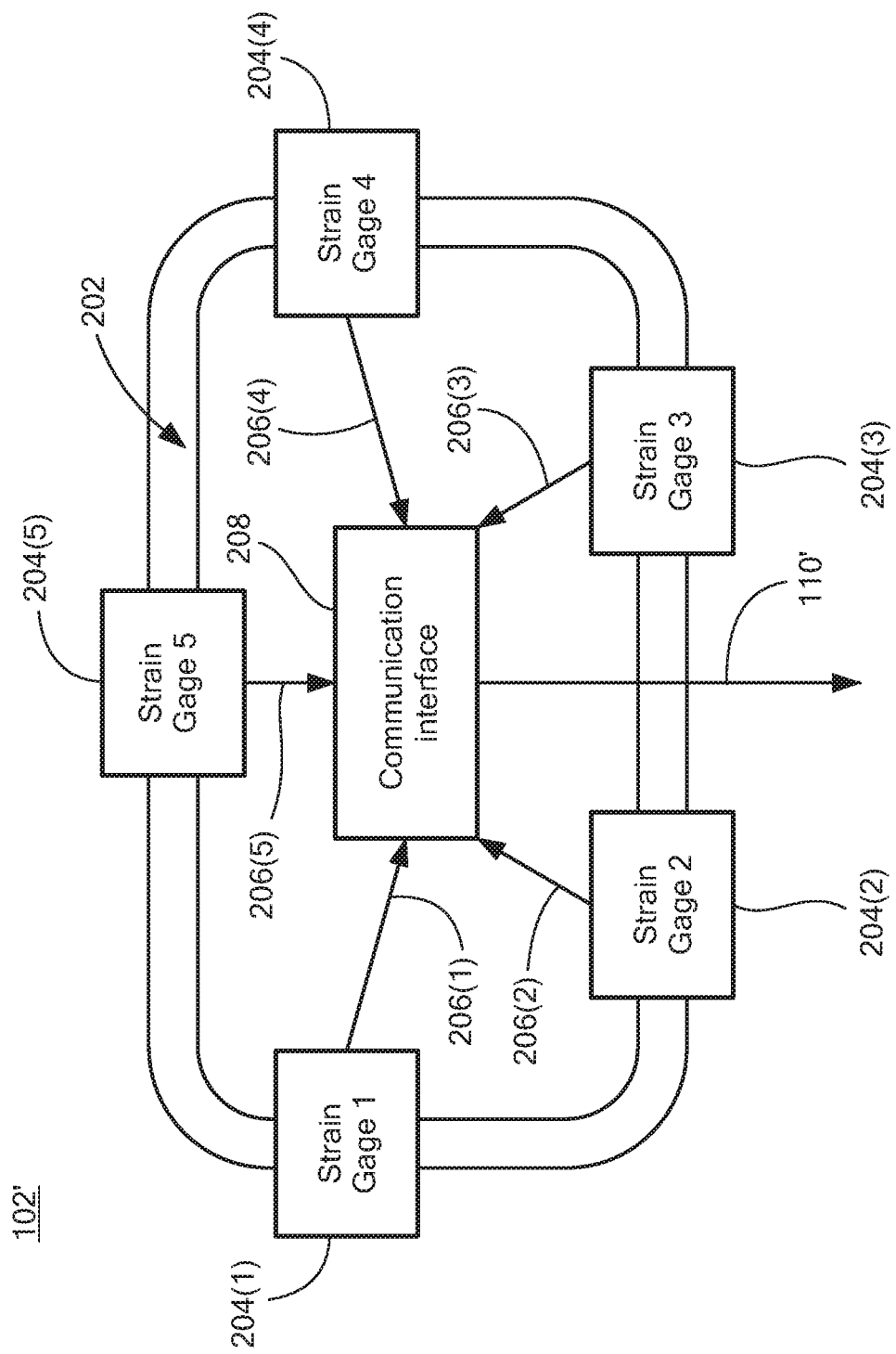
FIG. 2 is a block diagram of a load sensor suitable for use in a directional force sensing system such as the system of FIG. 1.

Referring now to FIG. 2, a directional force sensor 102' which may be the same as or similar to directional force sensor 102 described above in conjunction with FIG. 1 includes a leaf spring 202 having one or more force sensors 204, here five force sensors 204(1)-204(5), generally denoted 204 disposed thereon. In this example embodiment leaf spring 202 is illustrated as a generally circular wave washer and five force sensors 204 are provided as strain gages although other types of force sensors 204 may also be used. Although shown as including five strain gages disposed substantially symmetrically around a circumference of a generally circular wave washer 202, other leaf spring shapes and other numbers and arrangements of strain gages 204 may be employed.

The number and arrangement of sensors 204 to use in any particular application may be selected in accordance with a variety of factors including, but not limited to surface area of application, hardness/elasticity of surface, magnitude of force, durability/longevity requirements of application, desired granularity of data (sensors/per unit area), irregularity of surface, flexibility of surface. After reading the disclosure provided herein, those of ordinary skill in the art will appreciate how to select the number and arrangement of sensors on a leaf spring to suit the needs of a particular application.

Placing strain gages 204 in separate channels around wave washer or leaf spring 202 allows for identification of the direction that experiences a highest relative force among all of strain gages 204. Thus, directional force sensing element 102' can sense a direction of an applied force in addition to a magnitude of the applied force.

As shown in FIG. 2, each strain gage 204 may be in communication with communication interface 208 via strain gage outputs 206(1)-206(5), referred to generally as strain gage outputs 206. In some embodiments, strain gage outputs 206 may be implemented as a flex circuit coupled between wave washer 202 and a rigid circuit board for communication interface 208. Communication interface 208 may transmit data from strain gages 204 to aggregator 104 or controller 106 via communication link 110'. For example, interface may convert analog outputs of each of strain gages 204 to digital values. As described, in some embodiments, communication link 110' may be a SPI link.

Viscoelastic materials exhibit properties of both viscous and elastic materials when subjected to mechanical stress. This is because the entire sensor may be encased in a viscoelastic material such as a polymeric organosilicon compound such as polydimethylsiloxane (PDMS). It should be appreciated that without the encasing material, the system is not viscoelastic. It should also be appreciated that in preferred embodiments viscoelastic modeling and calibration may be performed so as to improve system performance (e.g. increase accuracy of measurements made by the system). Due to the presence of viscous characteristics, viscoelastic materials respond non-linearly to mechanical loading with respect to time. To mathematically model the stress and strain responses of viscoelastic materials, models reduce a viscoelastic material to a combination of springs to characterize the elastic response, and dashpots to characterize the viscous response, arranged in parallel, series, or combinations thereof.

As described herein, directional force sensor 102 may include a flexible leaf spring such as wave washer 202, with one or more strain gages 204 adhered to a perimeter or circumference of the wave washer. A rigid-flex circuit (e.g., the combination of strain gage outputs 206 and communication interface 208) may be suspended in the middle of wave washer 202 via flexible support members (or arms). In example embodiment, five flexible arms extend from communication interface 208 as a flexible circuit to connect to each strain gage 204.

Figure 3A:
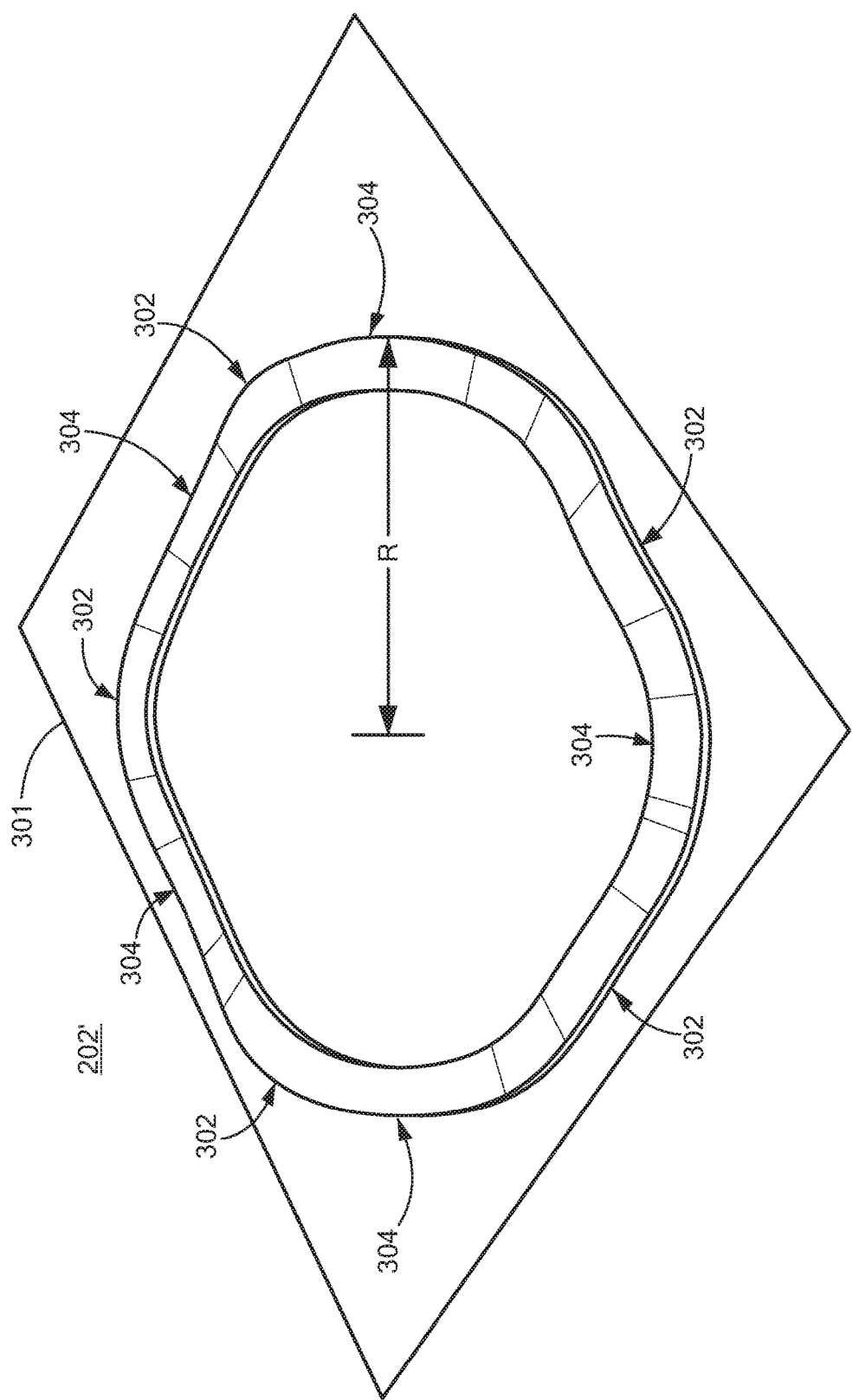
FIG. 3A is an isometric view of an illustrative wave washer suitable for use in a load sensor such as the load sensor describe above in conjunction with FIG. 2.

Referring now to FIG. 3A, an illustrative wave washer 202' which may be the same as or similar to wave washer 202 described above in conjunction with FIG. 2, is provided having a generally oval shape, here a generally circular shape having a radius R. It should, of course be appreciated that other shapes including, but not limited to regular geometric shapes (e.g. rectangular, square, triangular) and irregular geometric shapes may also be used. The particular size and shape of leaf spring to use in any particular application is selected in accordance with a variety of factors including, but not limited to surface area of application, hardness/elasticity of surface, magnitude of force, durability/longevity requirements of application, desired granularity of data (sensors/per unit area), irregularity of surface, flexibility of surface. It should also be appreciated that the spring may be provided having an open shape (e.g. a C-shape) as well as a linear shape. After reading the disclosure provided herein, those of ordinary skill in the art will appreciate how to select the size and shape of a leaf spring to suit the needs of a particular application.

With respect to a surface of a plane 301, wave washer 202' has raised portions 302 (i.e. portions above the surface of plane 301) and lowered portions 304 (i.e. portions below the surface of plane 301), thus proving the wave washer 202' having an undulating (or wave) pattern or shape. As will be described, each of the strain gages 204 of FIG. 2 may be disposed or otherwise fastened or secured to wave washer 202' at corresponding ones of either raised portions 302 or lowered portions 304 of wave washer 202'.

Figure 3B:
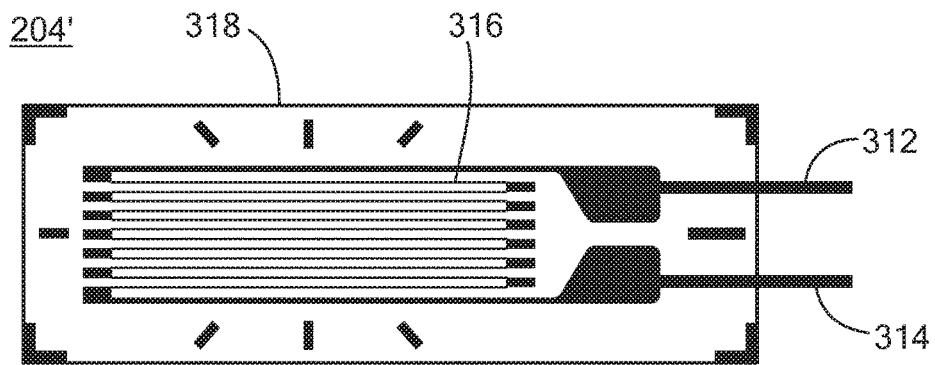
FIG. 3B is a top view of an illustrative force sensor suitable for use in a load sensor such as the load sensor described above in conjunction with FIG. 2.

Referring now to FIG. 3B, an illustrative strain gage 204' is shown. As shown, strain gage 204' includes a first lead 312 and a second lead 314, across which a resistance can be measured. Grid 316 is disposed upon carrier 318. Carrier 318 may be provided as any type of substrate on which grid 316 may be disposed. Carrier 318 is subject to strain force, which is transferred (and sometimes directly transferred) to grid 316 (grid can be sized (length, width, grid pattern) to size of sensor. As strain is applied to grid 316, the resistance of grid 316 and, thus, the resistance measured across leads 312 and 314, changes.

Figure 3C:
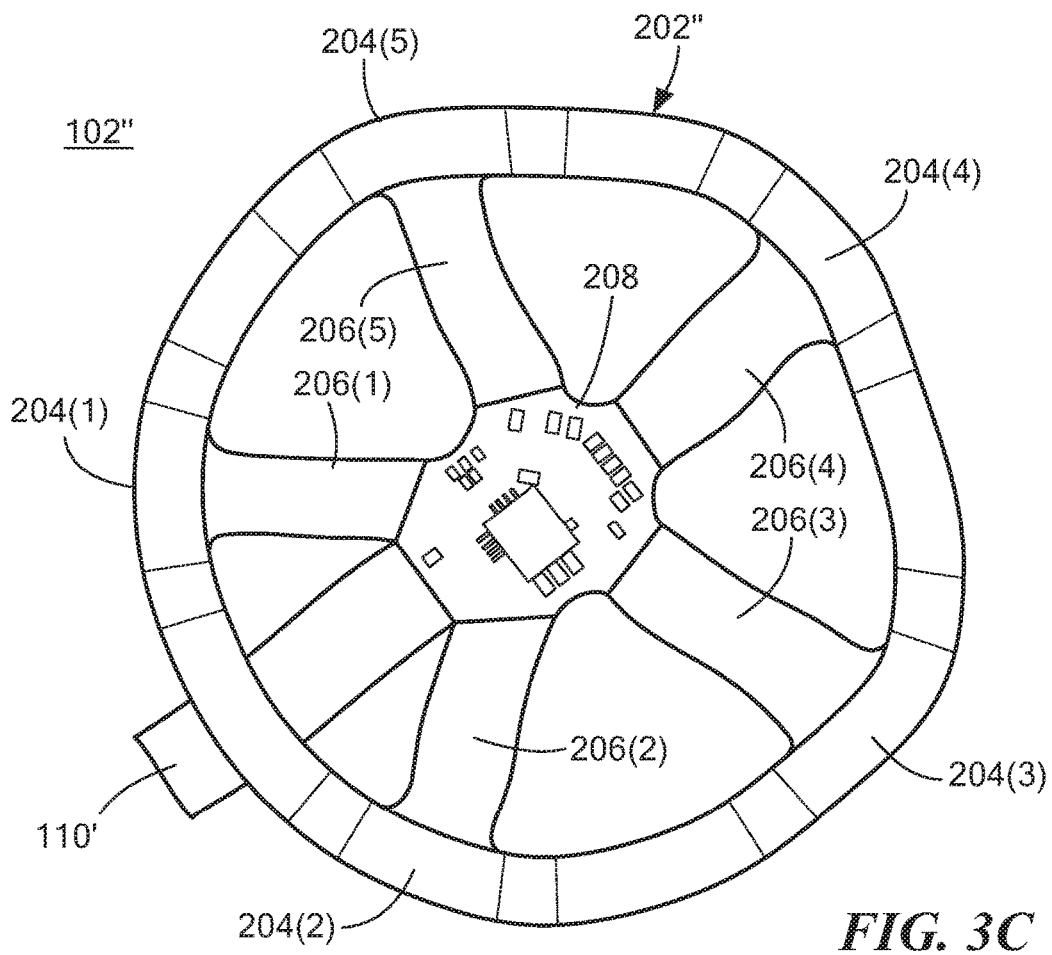
FIG. 3C is a top view of an illustrative load sensor suitable for use in a directional force sensing system such as the directional force sensing system of FIG. 1.

Referring to now to FIG. 3C, an illustrative directional force sensor 102" which may be the same as or similar to directional force sensors 102, 102' described above in conjunction with FIGS. 1 and 2 includes one or more strain gages 204 adhered or otherwise disposed about a portion of a wave washer 202". A rigid-flex circuit (e.g., the combination of strain gage outputs 206 and communication interface 208) is disposed in a generally central portion of wave washer 202". In this illustrative embodiment, a plurality of member (or "arms"), here five flexible arms 206(1)-206(5) extend from communication interface 208 as a flexible circuit coupled to each strain gage 204 so as to suspend communication interface 208 in a generally central portion (here a middle portion) of wave washer 202". It should be appreciate that, in some embodiment, it may be desirable or even necessary to have a number of arms which is different from the number of sensors (i.e. the number of arms could be either greater than, less than, or equal to the number of sensors). Multiple sensors could be connected to one or more arms.

When a strain gage is mounted on a leaf spring, such as a wave washer 202, the strain gage's resistance changes as a function of the flex of the wave washer. The total resistance of the strain gage can be expressed as the unloaded resistance, $R_{base}$, combined with a change in resistance, $\delta R$, which occurs when a force is applied to the strain gage. The total resistance is proportional to the force applied to the strain gage. For example, the total strain gage resistance may be given as $(R_{base}+\delta R) \propto$ Force.

Each of the strain gages shown in FIGS. 2 and 3C may be in communication with a separate analog-to-digital converter (ADC) channel of communication interface 208.

Figure 4:
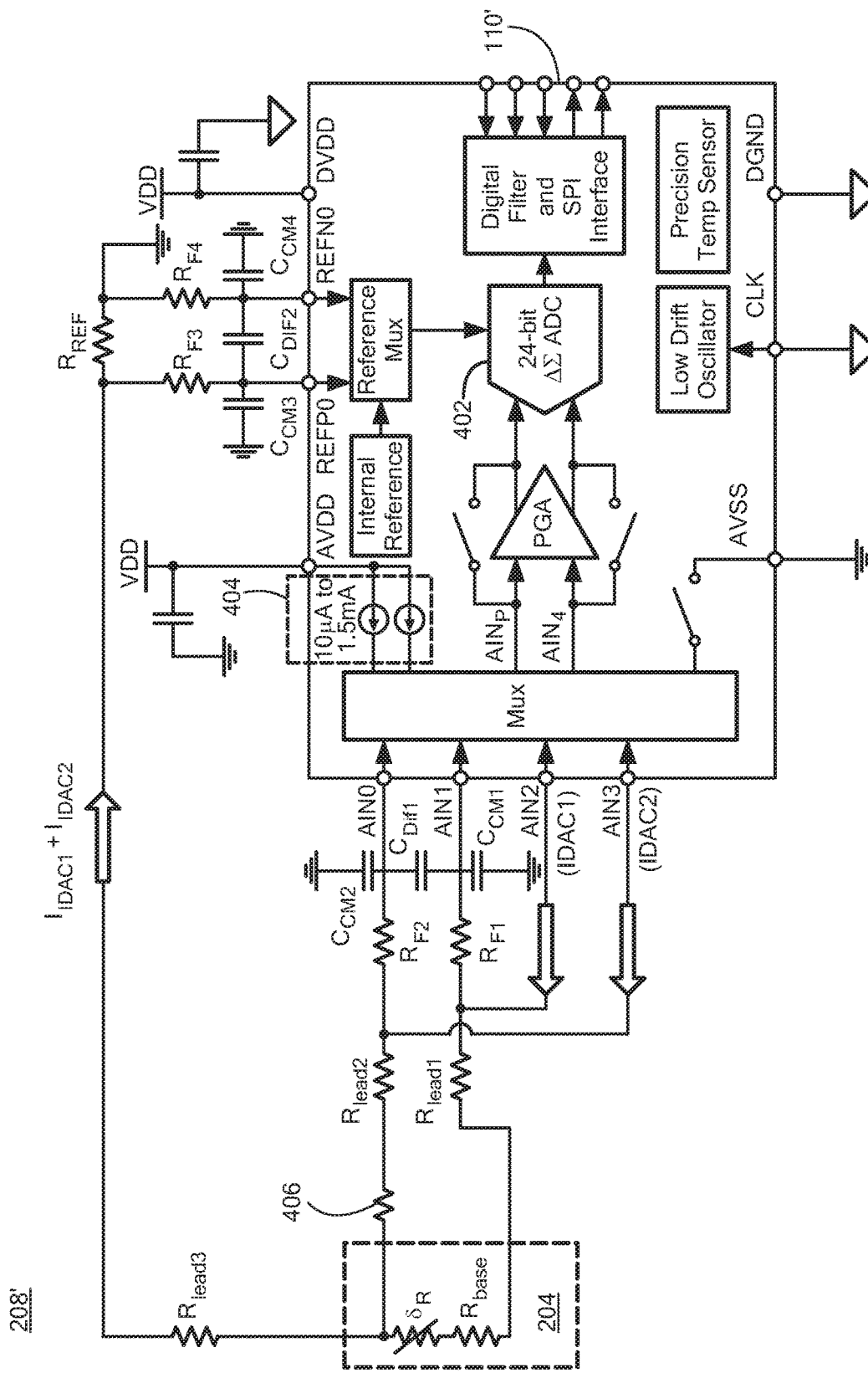
FIG. 4 is a schematic diagram of an illustrative communications circuit suitable for use in a load sensor such as the load sensor described above in conjunction with FIG. 2.

Referring now to FIG. 4, additional detail of communication interface 208 is shown as illustrative communication interface 208'. As shown in FIG. 4, communication interface 208' may include ADC 402 coupled with a measurable current source 404. In this example, ADC 402 employs a three-wire resistance measurement configuration to ratiometrically measure the variable resistance of each strain gage 204. In described embodiments, a resistance characteristic of the strain gage may vary by an amount which is a relatively small amount compared with the total resistance of the strain gage. For example, with a strain gage having an unloaded resistance, $R_{base}=350\Omega$, the change in resistance, $\delta R$, might be only 5-6$\Omega$ (~1.4%) over a 500 pound (LB) range of force applied to wave washer 202. Even if ADC 402 is a high-resolution ADC, many of the bits in a digitized signal provided by ADC will go towards measuring the relatively large base resistance, $R_{base}$, of the strain gage.

Thus, described embodiments may include one or more compensation resistors 406 to one of the inputs to the ADC. In some embodiments, compensation resistor 406 has a value, $R_{COMP}=R_{base}+\delta R/2$. Adding such a compensation resistor 406, the ADC effectively sees only the strain gage's change in resistance and not the base resistance value. Thus, the ADC can more accurately measure the force applied to the strain gage by more accurately measuring the change in resistance as force is applied.

In a three-wire resistance measurement configuration, the input leads of the circuit are usually resistance matched (e.g., shown here by resistors $R_{lead1}$ and $R_{lead2}$) by, for example, length matching the leads, so that the inherent resistance of the leads cancels out. The differential input voltage across the ADC inputs (AIN0 and AIN1) may be given by: $V_{in}=I_{IDAC1}*[R_{base}+\delta R+R_{lead1}]-I_{IDAC2}*[R_{base}+\delta R/2+R_{lead2}]$. If the current sources are matched such that $I_{IDAC1}=I_{IDAC2}=I_{IDAC}$, and if the lead resistances are also matched so that $R_{lead1}=R_{lead2}$, the lead resistances will cancel out. Thus, $V_{in}=I_{IDAC}*[R_{base}+\delta R]-I_{IDAC}*[R_{base}+\delta R/2]=I_{IDAC}*(\delta R/2)$. Thus, the base resistance of the strain gage can be effectively subtracted out from the view of the ADC, which allows the ADC to only measure the change in resistance of the strain gage, $\delta R$. In some embodiments, $\delta R$ may be in the range of 2.5-3$\Omega$.

Measuring only the change in resistance allows for more accurate measurements of applied force. The full-scale range (FSR) of the ADC ranges from negative FSR to positive FSR. However, by employing a compensation resistor having a value equal to the strain gage base resistance plus half of the strain gage's dynamic resistance (e.g., $R_{base}+\delta R/2$), the measured resistance change will go from zero to positive FSR and the input voltage, Vin, will go negative for half of the strain gage's change in resistance and positive for the other half, allowing $\delta R$ to be measured over the entire FSR. Using the entire full-scale range to measure only the $\delta R$ part of the strain gage maximizes the resolution with which ADC 402 can detect the gage's change in resistance.

FIG. 4 shows ADC 402 coupled to a single strain gage 204. In other words, FIG. 4 shows a single channel of ADC 402. As described herein, in some embodiments, each strain gage 204 may be coupled to its own channel of ADC 402, thus yielding directionality to the force measurement. In other embodiments, strain gages 204 could be connected in series to yield a total weight measurement on the wave washer.

In the illustrative embodiment of FIG. 4, strain gage 204 is coupled via a plurality of resistors and capacitors to ADC 402 which may, for example, be provided as the type available from Texas Instruments and identified as an ADS 1220 Low-Power, Low-Noise, 24-Bit, ADC for Small-Signal Sensors, having characteristics as provided in ADS1220 datasheet, May 2013 [Revised February 2015]. Other ADCs having the same or similar characteristics, may of course, also be used.

Directional force sensing element 102 can be adapted for different anticipated forces by varying the size and flexibility or orientation of the leaf spring or wave washer. The number of strain gages placed around the spring can also vary, allowing for adjustment of the directional resolution.

In some embodiments, the wave washer may be embedded in a mixture of two silicon materials. The viscoelastic behavior of the two silicon materials and the elastic behavior of the wave washer spring combine to form a complex viscoelastic system. Applying force to the sensor causes strain gages adhered to the wave washer to vary in resistance that can be measured over time. Strain is related to a strain gage's change in resistance by the Gage Factor, which is a constant property of the metal used in the strain gage (e.g., to form grid 316), and the un-deformed resistance of the strain gage, $R_{base}$. Since the Gage Factor and the un-deformed resistance both remain constant for a given strain gage, the change in resistance, $\delta R$, is linearly related to the strain, $\gamma$. Further, a viscoelastic material's strain changes non-linearly with time when a constant force is applied. However, over a small period of time, the change in strain is approximately linear.

Figure 5:
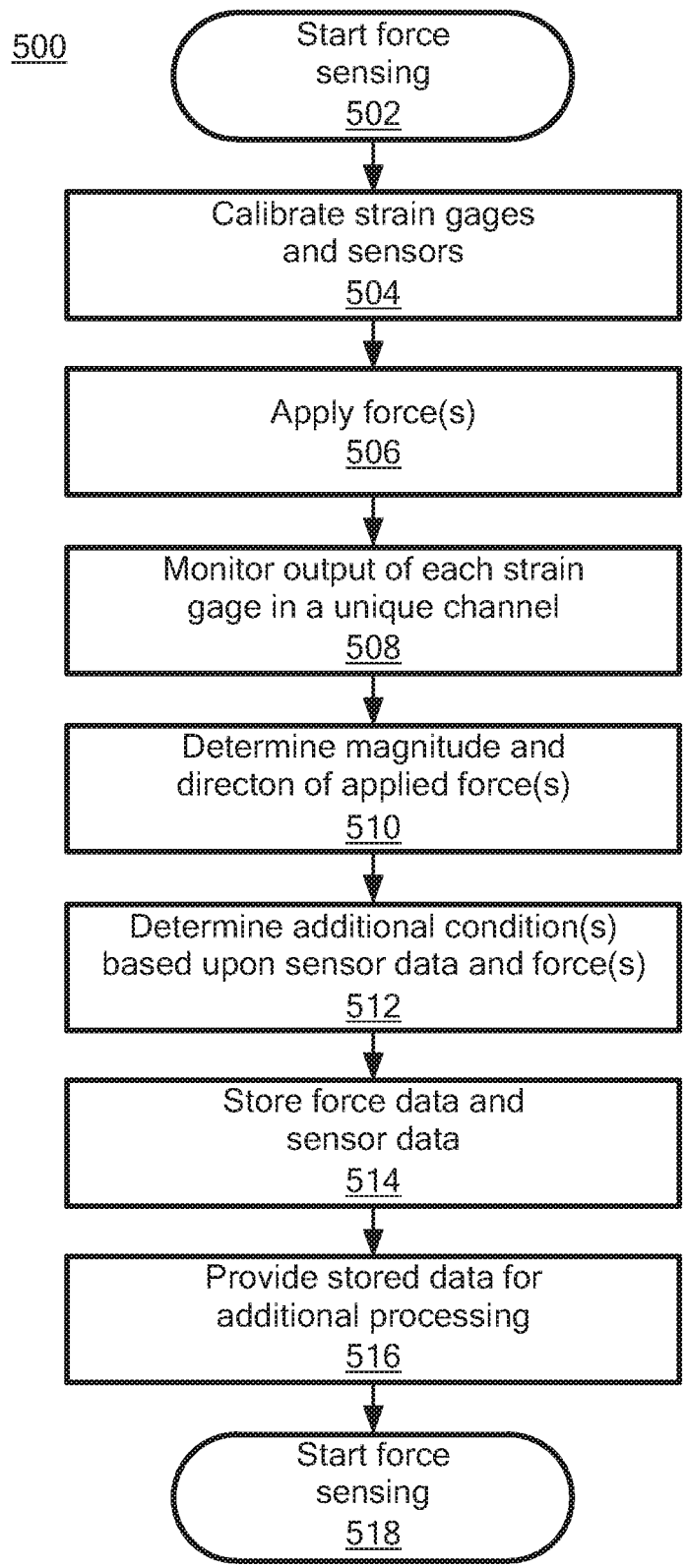
FIG. 5 is a flow diagram showing an illustrative process for detecting a directional force via a directional force sensing system such as the directional force sensing system described above in conjunction with FIG. 1.

FIG. 5 is a flow diagram showing illustrative processing that can be implemented within a directional force sensing element and/or within a directional force sensing system, such as the illustrative sensing elements and sensing systems described above in conjunction with FIGS. 1-4. Rectangular elements are herein denoted "processing blocks," and represent computer software instructions or groups of instructions. Alternatively, the processing blocks may represent steps or processes performed by functionally equivalent circuits such as a digital signal processor circuit or an application specific integrated circuit (ASIC). The flow diagram does not depict the syntax of any particular programming language, but rather illustrates the functional information one of ordinary skill in the art requires to fabricate circuits or to generate computer software to perform the processing described. It should be noted that many routine program elements, such as initialization of loops and variables and the use of temporary variables are not shown. It will be appreciated by those of ordinary skill in the art that unless otherwise indicated herein, the particular sequence of blocks described is illustrative only and can be varied without departing from the spirit of the concepts, structures, and techniques sought to be protected herein. Thus, unless otherwise stated the blocks described below are unordered, meaning that, when possible, the functions represented by the blocks can be performed in any convenient or desirable order.

Referring now to FIG. 5, a flow diagram of illustrative process 500 for operating directional force sensing system 100 is shown. At block 502, process 500 begins, for example when directional force sensing system 100 is powered on. At block 504, the load sensors (e.g., strain gages 204) and additional sensors (e.g., 118) are calibrated (e.g., to zero) prior to testing). At block 506, testing begins, for example by applying test force(s) to directional force sensors 102. At block 508, the output of each load sensor (e.g., strain gage 204) may be monitored in a separate channel of an ADC of system 100.

At block 510, a magnitude and/or direction of force applied to directional force sensor 102 is determined, for example based upon the digital output of each ADC channel. At block 512, additional environmental conditions of system 100 may be determined, for example based upon conditions sensed by sensors 118. For example, output from sensors 118 may be combined with force data sensed by directional force sensors 102 to determine stride data of a wearer of the footwear, a ground reaction force applied to the footwear, a foot-to-ground contact time of the footwear, a terrain map of terrain encountered by the wearer of the footwear, a contact angle of the footwear to the ground, a flexion angle of a leg of the wearer of the footwear, and an energy expenditure of the wearer of the footwear.

At block 514, sensor data and force data may be stored, for example in memory 122. At block 516, the stored data may be communicated to one or more remote processors, for example via communication interface 124. At block 518, process 500 completes.

As used in this application, the term "illustrative" is used herein to mean serving as an example, instance, or illustration. Any aspect or design described herein as "illustrative" is not necessarily to be construed as preferred or advantageous over other aspects or designs. Rather, use of the term "illustrative" is intended to present concepts in a concrete fashion. The phrase "in an embodiment" does not necessarily all refer to the same embodiment, nor are separate or alternative embodiments necessarily mutually exclusive.

To the extent directional terms are used in the specification and claims (e.g., upper, lower, parallel, perpendicular, etc.), these terms are merely intended to assist in describing the embodiments and are not intended to limit the claims in any way. Such terms, do not require exactness (e.g., exact perpendicularity or exact parallelism, etc.), but instead it is intended that normal tolerances and ranges apply. Similarly, unless explicitly stated otherwise, each numerical value and range should be interpreted as being approximate as if the word "about", "substantially" or "approximately" preceded the value of the value or range.

It should be understood that the steps of the illustrative methods set forth herein are not necessarily required to be performed in the order described, and the order of the steps of such methods should be understood to be provided as examples. Likewise, additional steps may be included in such methods, and certain steps may be omitted or combined, in methods consistent with various embodiments.

It will be further understood that various changes in the details, materials, and arrangements of the parts that have been described and illustrated herein might be made by those skilled in the art without departing from the scope of the following claims.

We claim:

1. An apparatus for measuring a directional force, the apparatus comprising:
 a leaf spring;
 one or more load sensors disposed or said leaf spring such that in response to a force applied to said leaf spring, said one or more load sensors provide a signal at an output thereof; and
 an analog-to-digital converter (ADC) coupled to receive signals from said one or more load sensors wherein a digital output of each channel of the ADC is employed to determine a magnitude and a direction of a force applied to the directional force sensor; and
 wherein said leaf spring is provided as a wave washer having an undulating surface and said one or more load sensors are disposed on said wave washer so as to form a directional force sensor.

2. The apparatus of claim 1, wherein said wave washer is provided having a generally oval shape.

3. The apparatus of claim 1, wherein said wave washer is provided having a generally circular shape.

4. The apparatus of claim 1, wherein said one or more load sensors are disposed on a surface of said wave washer.

5. The apparatus of claim 1, wherein said one or more load sensors are disposed around a perimeter of the leaf spring.

6. The apparatus of claim 1, wherein the force applied to the directional force sensor comprises perpendicular and shear forces.

7. The apparatus of claim 1, wherein each load sensor is coupled to a separate channel of said ADC.

8. The apparatus of claim 1, wherein the one or more load sensors comprise one or more strain gauges.

9. The apparatus of claim 8, wherein each of the one or more strain gauges has a base resistance value and the apparatus further comprises a compensation resistor coupled to said ADC, said a compensation resistor having a value selected to compensate for the base resistance value of each strain gauge, thereby measuring only a change in resistance of each strain gauge as force is applied to each strain gauge.

10. A system comprising:
a directional force sensor comprising:
- a leaf spring wherein said leaf spring is provided as a wave washer having an undulating surface;
- one or more load sensors disposed on said wave washer so as to form a directional force sensor such that in response to a force applied to said wave washer, said one or more load sensors provide a signal at an output thereof;

an analog-to-digital converter (ADC) coupled to receive signals from the one or more load sensors of each of said one or more directional force sensors; and a controller coupled to said one or more directional force sensors.

11. The system of claim 10 wherein said directional force sensor is a first one of a plurality of directional force sensors, each of said directional force sensors comprising:
a wave washer; and
one or more load sensors disposed on said wave washer such that in response to a force applied to said wave washer, said one or more load sensors provide a signal at an output thereof.

12. The system of claim 11, further comprising:
an aggregator coupled between each of said directional force sensors and said controller, said the aggregator configured to batch data from the one or more directional force sensors for communication to said controller.

13. The system of claim 12, wherein said controller comprises one or more sensors, each of the one or more sensors responsive to one or more environmental conditions in which the controller may be disposed.

14. The system of claim 13, wherein the one or more sensors comprise at least one of:
a temperature sensor;
a humidity sensor;
a magnetometer;
a gyrometer;
one or more accelerometers;
one or more motion sensors;
a global positioning system; and
an altimeter.

15. The system of claim 10, wherein the directional force sensor is disposed in footwear to sense a force applied to a sole of the footwear.

16. The system of claim 10, wherein the controller is configured to determine at least one of a stride data of a wearer of the footwear, a ground reaction force applied to the footwear, a foot-to-ground contact time of the footwear, a terrain map of terrain encountered by the wearer of the footwear, a contact angle of the footwear to the ground, a flexion angle of a leg of the wearer of the footwear, and an energy expenditure of the wearer of the footwear.

17. The system of claim 10, wherein the directional force sensor is implemented in at least one of a backpack, a mattress, a wheelchair, a CPR simulator, sports equipment, car seat, parachute, seatbelt, steering wheel, vehicle bumper, bridge support, footwear and anthropomorphic test devices.

* * * * *